(12) United States Patent  (10) Patent No.: US 6,466,256 B1
Takahashi et al.  (45) Date of Patent: *Oct. 15, 2002

(54) VIDEO-SIGNAL PROCESSING DEVICE CONNECTABLE TO AN ELECTRONIC ENDOSCOPE

(75) Inventors: Akihiro Takahashi; Kouhei Iketani, both of Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/833,254

(22) Filed: Apr. 4, 1997

(30) Foreign Application Priority Data

Apr. 5, 1996 (JP) .............................. 8-110269
Apr. 15, 1996 (JP) ............................ 8-117086

(51) Int. Cl.$^7$ ................................ H04N 7/18
(52) U.S. Cl. ...................................... 348/71; 348/74
(58) Field of Search ...................... 250/201.9; 348/45, 348/65, 68–74, 222; 600/101, 109; H04N 7/18

(56) References Cited

U.S. PATENT DOCUMENTS 4,716,457 A * 12/1987 Matsuo ........................ 348/71
4,853,772 A * 8/1989 Kikuchi ...................... 600/109
4,924,856 A * 5/1990 Noguchi ..................... 600/109
4,950,880 A * 8/1990 Hayner ..................... 250/201.9
5,138,458 A * 8/1992 Nagasaki et al. ........... 348/222
5,305,098 A * 4/1994 Matsunaka et al. .......... 348/65
5,374,953 A * 12/1994 Sasaki et al. ................. 348/65
5,696,553 A * 12/1997 D'Alfonso et al. ........... 348/45
5,864,361 A * 1/1999 Sekiya et al. ................. 348/70
5,877,802 A * 3/1999 Takahashi et al. ............ 348/71
5,902,230 A * 5/1999 Takahashi et al. .......... 600/109
5,929,899 A * 7/1999 Takahashi et al. ............ 348/65

* cited by examiner

Primary Examiner—Richard Lee
(74) Attorney, Agent, or Firm—Greenblum & Bernstein, P.L.C.

(57) ABSTRACT

A video-signal processing device is connectable to an electronic endoscope designed to output at least one kind of electric analog video signal, and comprises: an analog-to-digital converter for converting the electric analog video signal into a parallel electric digital video signal; and a parallel-to-serial converter for converting the parallel electric digital video signal into a serial electric digital video signal, whereby the electric analog video signal outputted from the electronic endoscope is fed outside from said device as the serial electric digital video signal.

9 Claims, 14 Drawing Sheets

VIDEO-SIGNAL PROCESSING DEVICE CONNECTABLE TO AN ELECTRONIC ENDOSCOPE

BACKGROUND OF THE INVENTION

1. Field of the Invention

The present invention relates to a video-signal processing device connectable to an electronic endoscope, and more particularly relates to a video-signal processing device that intervenes between an electronic endoscope and peripheral equipment such as a television (TV) monitor, a video tape recorder, a printer, a video-image processing computer, and so on.

2. Description of the Related Art

The described electronic endoscope comprises a flexible conduit and a video processor to which the flexible conduit is detachably joined.

The flexible conduit has an objective lens system provided at the distal end thereof, and a solid state image sensor such as a CCD (charge-coupled device) associated therewith. An object to be photographed is focused, as an optical image, on a light receiving surface of the CCD image sensor by the objective lens system. The optical image is converted into analog image-pixel signals by the CCD image sensor, and the analog image-pixel signals are successively read out of the image sensor by a CCD driver circuit.

Also, the flexible conduit has an optical guide provided therewithin, and the optical guide terminates at a light-emitting end face at the distal end of the flexible conduit. The video processor also includes an optical guide provided therein. When the flexible conduit is joined to the video processor, one end of the optical guide of the video processor is connected to a proximal (base) end of the optical guide of the flexible conduit.

The video processor of the electronic endoscope also has a light source and a collective lens system associated therewith, and light rays emitted from the light source are focused on the other end face of the optical guide of the video processor by the collective lens system. Thus, a front area of the distal end of the flexible conduit is illuminated by the light rays emitted from the light-emitting end face of the optical guide of the flexible conduit.

For reproduction of a photographed image as a color image, for example, an RGB field sequential type color imaging system is introduced in the electronic endoscope. Namely, a rotary RGB color filter is intervened between the light source and the inner end face of the optical guide of the video processor, and the RGB color filter is rotated at a given frequency of rotation. In this manner, an object to be photographed is sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor by the CCD driver circuit are fed to the video processor, which processes the analog color-image pixel signals to thereby produce a color video signal. Usually, the video processor of the electronic endoscope is connected to a medical TV monitor designed to ensure electrical security, and a photographed image is reproduced on the medical TV monitor on the basis of the color video signal fed from the video processor thereto.

Also, the electronic endoscope may be connected to a consumer TV monitor at a medical site, for reproduction of a photographed image thereon, but in general the consumer TV monitor is not designed to ensure electrical security. In this case, "electrical security" means both confidentiality and the critical function of electrically insulating a patient from stray current on the signal lines.

On the other hand, it is sometimes desired to connect an electronic endoscope to other peripheral equipments (such as a video tape recorder, a printer, an image-processor and so on) other than a TV monitor. To this end, the video processor of the electronic endoscope is arranged to output at least two kinds of color video signals. However, in this case, of course, the peripheral equipment are not designed to ensure electrical security.

Furthermore, a user may want to connect the electronic endoscope to a peripheral remotely located from the electronic endoscope. For example, at a large hospital of more than two buildings, there may be a case where a color video signal must be fed from the electronic endoscope used in a room of a first building to a peripheral equipment located at a room of another building. In this case, the video signal should be fed as a digital video signal from the electronic endoscope to the peripheral because an analog video signal is susceptible to attenuation.

Nevertheless, the feeding of the digital video signal to the remote peripheral is not expedient because an expensive parallel signal cable having at least plural signal lines corresponding to a bit number of the digital video signal must be laid therebetween.

SUMMARY OF THE INVENTION

Therefore, an object of the present invention is to provide a video-signal processing device connectable to an electronic endoscope such that at least one kind of video signal is fed as a serial digital signal from the electronic endoscope to a peripheral equipment such as a TV monitor, a video tape recorder, a printer, an image-processor and so on therethrough, whereby the feeding of the video signal from the electronic endoscope to the peripheral equipment is possible without using an expensive signal cable having a plurality of signal lines.

Another object of the present invention is to provide a video-signal processing device of the above-mentioned type, wherein the feeding of an uncontrollable image in the video signal to the peripheral equipment can be prevented during the connection of the video-signal processing device to the electronic endoscope.

Yet another object of the present invention is to provide a video-signal processing device of the above-mentioned type, wherein the feeding of the image in the video signal to the peripheral equipment can be forcibly stopped, if necessary.

Furthermore, another object of the present invention is to provide a video-signal processing device of the above-mentioned type, wherein the feeding of the image in the video signal to the peripheral equipment is possible in such a manner that the electronic endoscope is electrically insulated from the video-signal processing for electrical security and to protect a patient from stray current on the signal lines.

In accordance with an aspect of the present invention, there is provided a video-signal processing device connectable to an electronic endoscope designed to output at least one kind of electric analog video signal, the device comprising: an analog-to-digital converter for converting the electric analog video signal into a parallel electric digital video signal; and a parallel-to-serial converter for converting the parallel electric digital video signal into a serial electric digital video signal, whereby the electric analog video signal outputted from the electronic endoscope is fed outside from the device as the serial electric digital video signal.

The video-signal processing device may further comprise: an electrical-optical converter for converting the serial electric digital video signal into a serial optical digital video signal; a manual switch for forcibly stopping the feeding of the serial electric digital video signal from the device; and a insulation coupler for making it possible to input the electric analog video signal from the electronic endoscope to the device, whereby the electronic endoscope is electrically insulated from the device. The insulation coupler may be a photo-coupler or a transformer coupler.

In accordance with another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and at least three kinds of video-signal-components, the device comprising: an analog-to-digital converter for converting the video-signal-components into parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

The video-signal processing device may further comprise: an electrical-optical converter for converting the serial electric digital video-signal-components into serial optical digital video-signal-components; a manual switch for forcibly stopping the outputting of the serial video-signal-components from the device; an insulation coupler for making it possible to input the component-type electric analog color video signal from the electronic endoscope to the device, whereby the electronic endoscope is electrically insulated from the peripheral equipment.

Furthermore, the video-signal processing device may comprise: a phase-lock detector for detecting the coincidence of the phase of the clock pulses with the phase of the composite synchronizing signal; a signal-output stopper for stopping the outputting of the serial digital video-signal-components from the device until the phase-lock detector detects the coincidence of the phase of the clock pulses with the phase of the composite synchronizing signal; and an electrical-optical converter for converting the serial electric digital video-signal-components into serial optical digital video-signal-components.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a red video-signal-component, a green video-signal-component, and a blue video-signal-component, the device comprising: a color-conversion analog matrix circuit for producing a luminance signal-component, and two kinds of color-difference signal components on the basis of the read, green, and blue video-signal-components; an analog-to-digital converter for converting each of the luminance signal-component, and the two kinds of color-difference signal components into a parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a red video-signal-component, a green video-signal-component, and a blue video-signal-component, the device comprising: an analog-to-digital converter for converting each of the red, green, and blue video-signal-components into a parallel digital color video-signal-component; a color-conversion digital matrix circuit for producing a parallel digital luminance signal-component, and two kinds of parallel digital color-difference signal-components on the basis of the parallel digital color video-signal components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are out putted outside at proper timing from the device.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a luminance signal-component, and two kinds of color-difference signal components, the device comprising: an analog-to-digital converter for converting each of the luminance signal-component, and the two kinds of color-difference signal components into a parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

In accordance with yet another aspect of the present invention, there is provided a video-signal processing device connectable to an electronic endoscope designed to output at least two kinds of video signals, the device comprising: a switch circuit provided in output-signal lines for the two kinds of video signals; and respective manual switches corresponding the two kinds of video signals for operating the switch circuit in such a manner that an outputting of one of the two kind of video signals from the device is forcibly stopped when turning ON the corresponding manual switch.

In accordance with yet another aspect of the present invention, there is provided a video-signal processing device connectable to an electronic endoscope designed to output at least one kind of video signal, and a plurality of control signals for a video image processing computer, the device comprising: an analog-to-digital converter for converting the electric analog video signal into a parallel electric digital video signal; a parallel-to-serial converter for converting the parallel electric digital video signal into a serial electric digital video signal, whereby the electric analog video signal outputted from the electronic endoscope is fed outside from the device as the serial electric digital video signal; and a processing circuit for processing a command signal, fed from the video-image processing computer to the device, for stopping the feeding of the serial electric digital video signal, whereby the feeding of the serial electric digital video signal is forcibly stopped upon receiving the command signal.

BRIEF DESCRIPTION OF THE DRAWINGS

The objects and other objects of the present invention will be better understood from the following description, with reference to the accompanying drawings in which.

DESCRIPTION OF THE PREFERRED EMBODIMENTS

Figure 1:
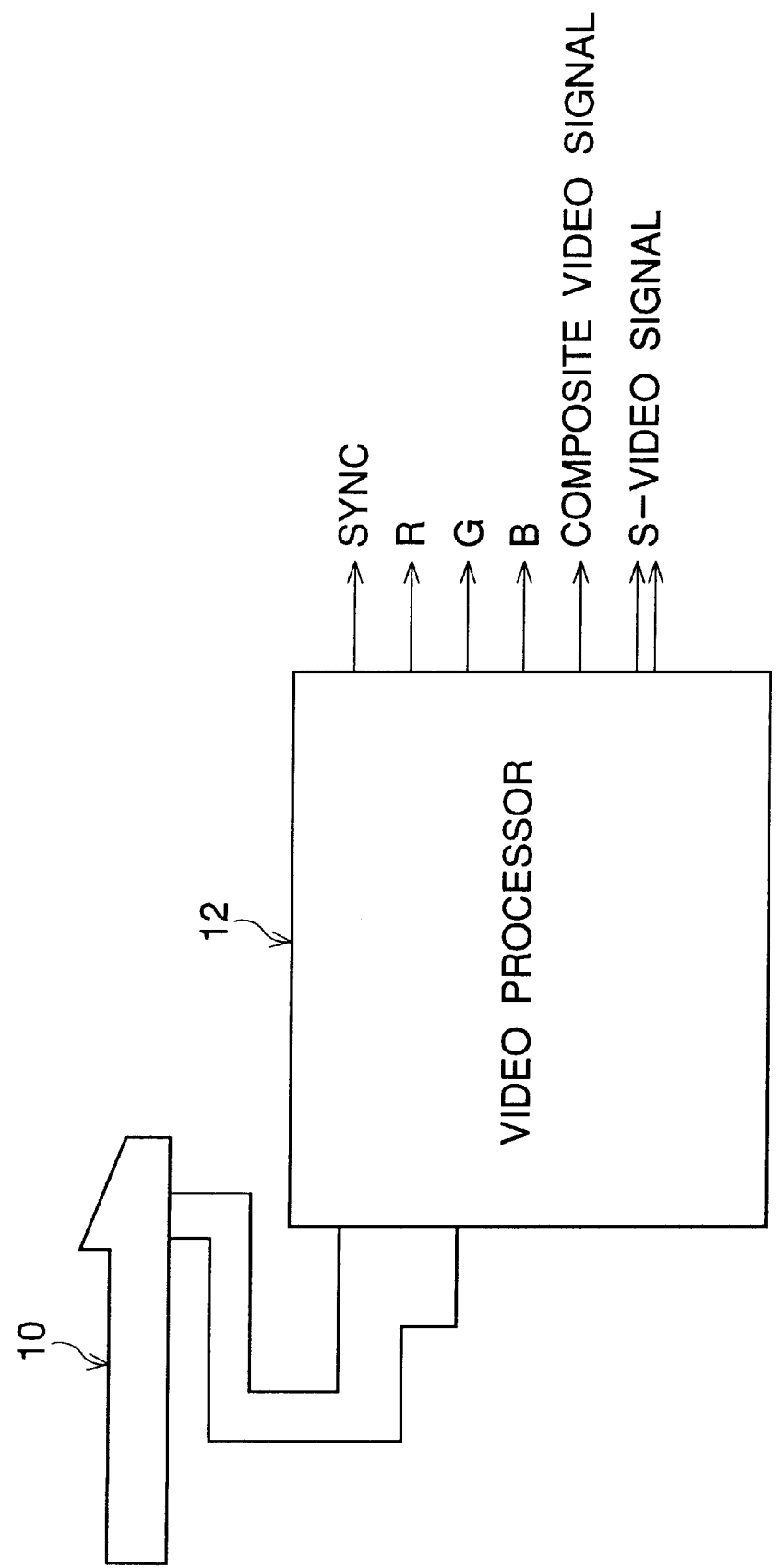
FIG. 1 is a schematic view showing an electronic endoscope to which a video-signal processing device according to the present invention may be connected.

FIG. 1 schematically shows an electronic endoscope, to which a video-signal processing device according to the present invention may be connected. The electronic endoscope includes a flexible conduit 10 and a video processor 12 to which the flexible conduit 10 is detachably joined.

The flexible conduit 10 has an objective lens system (not shown) provided at the distal end thereof, and a solid state image sensor such as a CCD (charge-coupled devices, not shown) associated therewith. An object to be photographed is focused as an optical image on a light receiving surface of the CCD image sensor by the objective lens system. The optical image is converted into analog image-pixel signals by the CCD image sensor, and the analog image-pixel signals are successively read out of the image sensor by a CCD driver circuit (not shown) therefor.

The flexible conduit 10 has an optical guide provided therewithin, and the optical guide (not shown) may be formed by a bundle of optical fibers. The optical guide terminates at a light-emitting end face at the distal end of the flexible conduit 10. The video processor 12 also includes an optical guide (not shown) provided therein, and this optical guide may be also formed by a bundle of optical fibers. When the flexible conduit 10 is joined to the video processor 12, one end of the optical guide of the video processor 12 is connected to a proximal (base) end of the optical guide of the flexible conduit 10.

The video processor 12 also has a light source (not shown), and a collective lens system (not shown) associated therewith, and light rays emitted from the light source are focused on the other end face of the optical guide of the video processor 12 by the collective lens system. Thus, a front area of the distal end of the flexible conduit 10 is illuminated by the light rays emitted from the light-emitting end face of the optical guide of the flexible conduit 10.

For reproduction of a photographed image as a color image, for example, an RGB field sequential type color imaging system (not shown) is introduced in the electronic endoscope. That is, a rotary RGB color filter intervenes between the light source and the inner end face of the optical guide of the video processor 12, and the RGB color filter is rotated at a given frequency of rotation. An object to be photographed is thereby sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor are fed to the video processor 12, and are then subjected to various image-processings such as white-balance processing, gamma-correction processing and so on. In the electronic endoscope shown in FIG. 1, three kinds of color video signals are produced on the basis of the processed color-image-pixel signals, and are output from the video processor 12.

That is, as shown in FIG. 1, as a first kind of color video signal, a component-type color video signal composed of a composite synchronizing signal (SYNC), a red video signal (R), a green video signal (G), and a blue video signal (B) is output from the video processor 12; as a second kind of color video signal, an S-video signal composed of a luminance signal and an amplitude-modulated (AM) color-difference signal is outputted from the video processor 12; and, as a third kind of color video signal, a composite color video signal combined with a luminance signal and an amplitude-modulated (AM) color-difference signal is outputted from the video processor 12.

Figure 2:
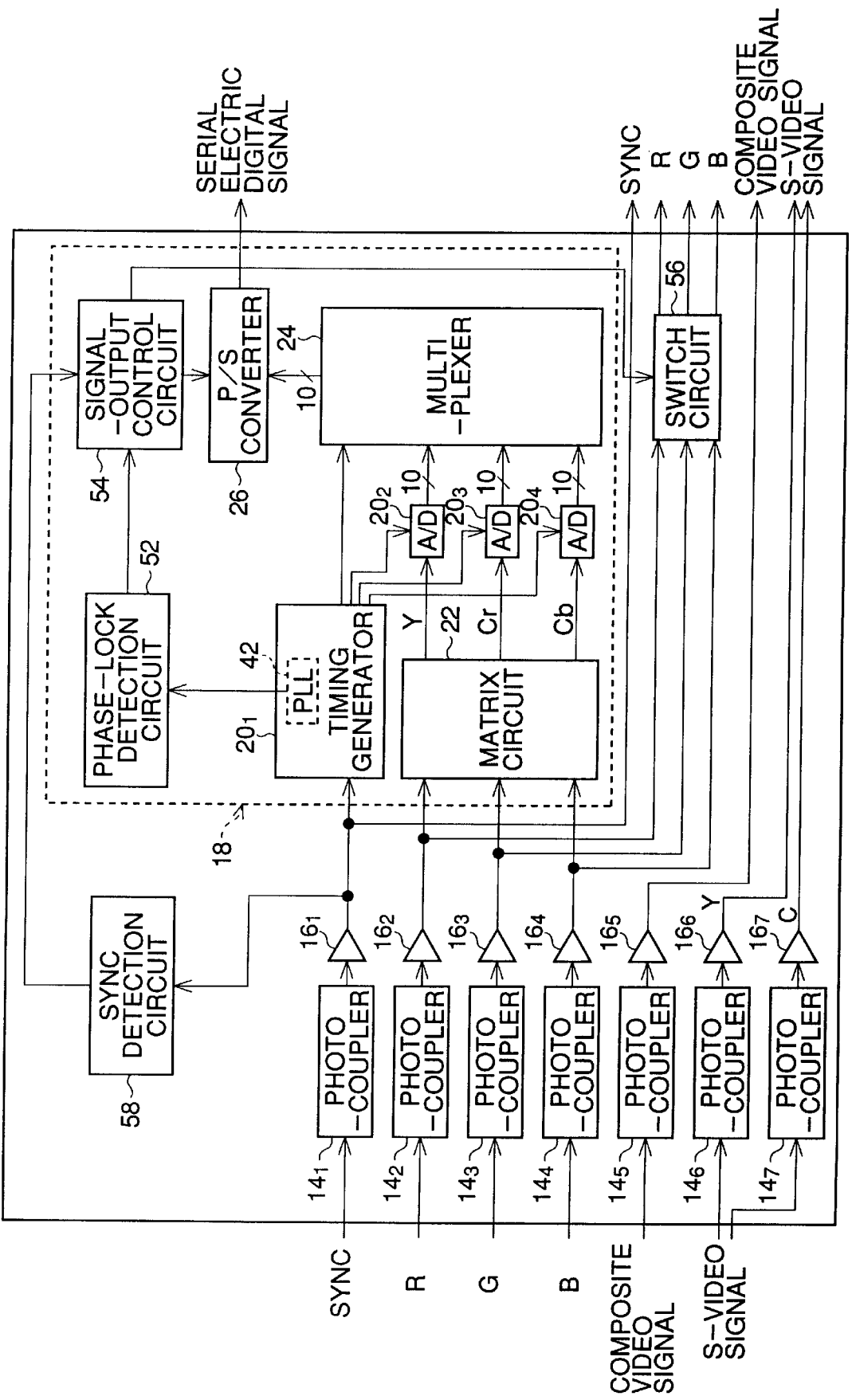
FIG. 2 is a block diagram showing a first embodiment of the video-signal processing device according to the present invention.

FIG. 2 shows a block diagram of a first embodiment of the video-signal processing device according to the present invention, which is connectable to the video processor 12 of the electronic endoscope shown in FIG. 1. The video-signal processing device comprises seven photo-couplers $14_1$ to $14_7$, and, when the video-signal processing device is connected to the video processor 12, the three kinds of video signals output from the video processor 12 are input to the seven photo-couplers $14_1$ to $14_7$.

In particular, the respective composite synchronizing signal (SYNC), red video signal (R), green video signal (G), and blue video signal (B) of the first kind of color video signal (the component-type color video signal) are inputted to the photo-couplers $14_1$ to $14_4$; the respective luminance signal and amplitude-modulated (AM) color-difference signal of the second kind of color video signal (the S-video signal) are inputted to the photo-couplers $14_6$ and $14_7$; and the third kind of color video signal, i.e., the composite color video signal combined with the luminance signal and the amplitude-modulated (AM) color-difference signal, is input to the photo-coupler $14_5$.

Each of the photo-couplers $14_1$ to $14_7$ once converts the inputted electric signal into a photo-signal, and then converts and outputs the photo-signal as an electric signal. Namely, the video-signal processing device is optically coupled to the video processor 12 of the electronic endoscope, whereby the electronic endoscope is electrically insulated from various peripheral equipment connected to the electronic endoscope via the video-signal processing device according to the present invention.

The respective composite synchronizing signal (SYNC), red video signal (R), green video signal (G), and blue video signal (B) output from the photo-couplers $14_1$ to $14_4$ are amplified by the amplifiers $16_1$ to $16_4$, and the amplified signals (SYNC, R, G, B) are input to a digital-conversion processing circuit 18 including a timing generator circuit $20_1$; three analog-to-digital (A/D) converters $20_2$, $20_3$, and $20_4$; a color-conversion matrix circuit 22; a multiplexer 24; and a parallel-to-serial(P/S) convertor 26.

In particular, the amplified composite synchronizing signal (SYNC) output from the amplifier $16_1$ is input to the timing generator circuit $20_1$, which produces a horizontal synchronizing signal, a vertical synchronizing signal, and several series of clock pulses having individual frequencies produced on the basis of the inputted composite synchronizing signal (SYNC).

Also, the respective amplified red video signal (R), green video signal (G), and blue video signal (B) output from the amplifiers $16_2$, $16_3$, and $16_4$ are input to the color-conversion matrix circuit 22, which produces a luminance signal (Y), and two kinds of color-difference signals $C_r$, $C_b$ ($C_r$=R−Y and $C_b$=B−Y) on the basis of the inputted color video signals (R, G, and B). Then, the luminance signal (Y), and the two kinds of color-difference signals ($C_r$ and $C_b$) are input to the A/D converters $20_2$, $20_3$, and $20_4$, in which the signals (Y, $C_r$, and $C_b$) are converted into 10-bit digital signals, respectively.

In this embodiment, the sampling of the 10-bit digital luminance signal (Y) from the A/D converter $20_2$ is carried out in accordance with a series of clock pulses of 13.5 MHz output from the timing generator circuit $20_1$. Also, the sampling of each 10-bit digital color-difference signal ($C_r$, $C_b$) from the A/D converters $20_3$ and $20_4$ is carried out in accordance with a series of clock pulses of 6.75 MHz output from the timing generator circuit $20_1$. Namely, the sampling frequency of the digital luminance signal is twice that of each digital color-difference signal ($C_r$, $C_b$).

The 10-bit digital signals (Y, $C_r$, and $C_b$) output from the A/D converters $20_2$, $20_3$, and $20_4$ are input to the multiplexer 24, which output the 10-bit digital signals (Y, $C_r$, and $C_b$) in regular sequence. In this embodiment, for example, the output of the 10-bit digital signals (Y, $C_r$, and $C_b$) may be sequentially carried out in the order of the luminance signal (Y), the color-difference signal ($C_r$), the luminance signal (Y), and the color-difference signal ($C_b$). In this case, e.g., the sequential output of the 10-bit digital signals (Y, $C_r$, and $C_b$) is based upon a series of clock pulses of 27 MHz outputted from the timing generator circuit $20_1$. It should be noted that the frequency of 27 MHz is twice the sampling frequency of 13.5 MHz of the luminance signal (Y).

In this embodiment, over an effective image-period of a horizontal scanning line, the sampling of the digital luminance signals (Y) is carried out 720 times, and each of the sampling of the respective color-difference signals ($C_r$ and $C_b$) is carried out $36_0$ times. Namely, a total sampling of 1,440 (720+2×360) of the digital signals (Y, $C_r$, and $C_b$) is obtained from the effective image-period of the horizontal scanning line.

Figure 3:
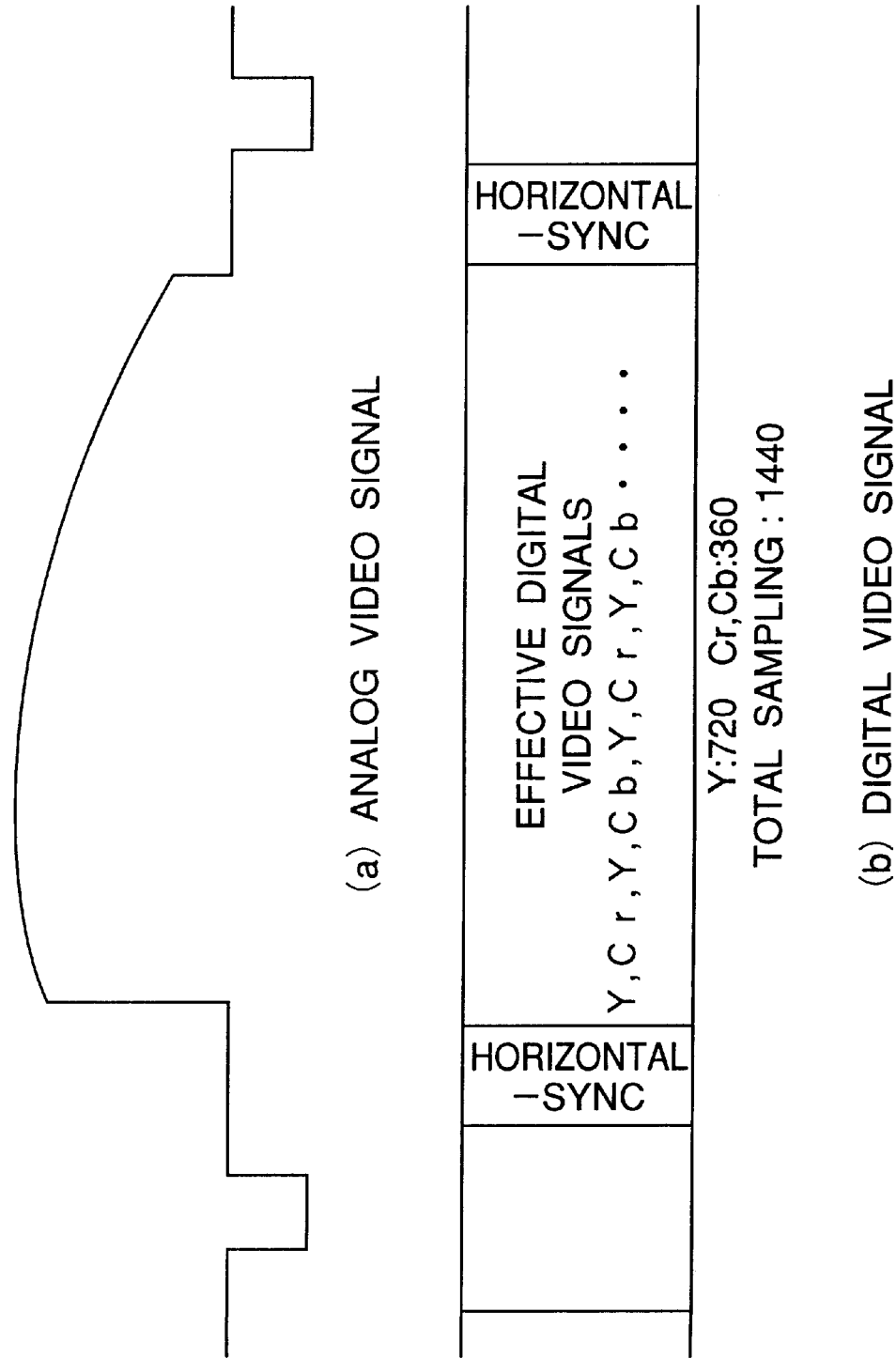
FIG. 3 is a conceptual view showing a relationship between an analog video signal of a horizontal scanning line and sampled digital signals obtained therefrom.

With reference to FIG. 3, a relationship between an analog video signal of a horizontal scanning line and sampled digital signals (Y, $C_r$, and $C_b$) obtained therefrom is conceptually shown.

If the 10-bit digital signal (Y, $C_r$, $C_b$) are directly fed from the multiplexer 24 to a peripheral, the video-signal processing device and the peripheral must be connected to each other through a parallel signal cable having at least eleven signal lines. In this case, ten signal lines of the signal cable would be used for the feeding of the 10-bit digital signal (Y, $C_r$, $C_b$), and the other single line thereof would be necessary for feeding a series of clock pulses. Of course, the use of a parallel signal cable having at least eleven signal lines is not preferable, especially when the peripheral equipment is not placed in site, i.e., when the peripheral equipment is remote from the place at which the electronic endoscope is used. That is, a parallel signal cable having a plurality of signal lines is expensive.

According to the present invention, the parallel 10-bit digital signal (Y, $C_r$, $C_b$) output from the multiplexer 24 is inputted to the parallel-to-serial (P/S) converter 26, which converts the parallel 10-bit digital signal (Y, $C_r$, $C_b$) into a serial 10-bit digital signal in accordance with a series of driving clock pulses having a given frequency and output from the timing generator circuit $20_1$.

Figure 4:
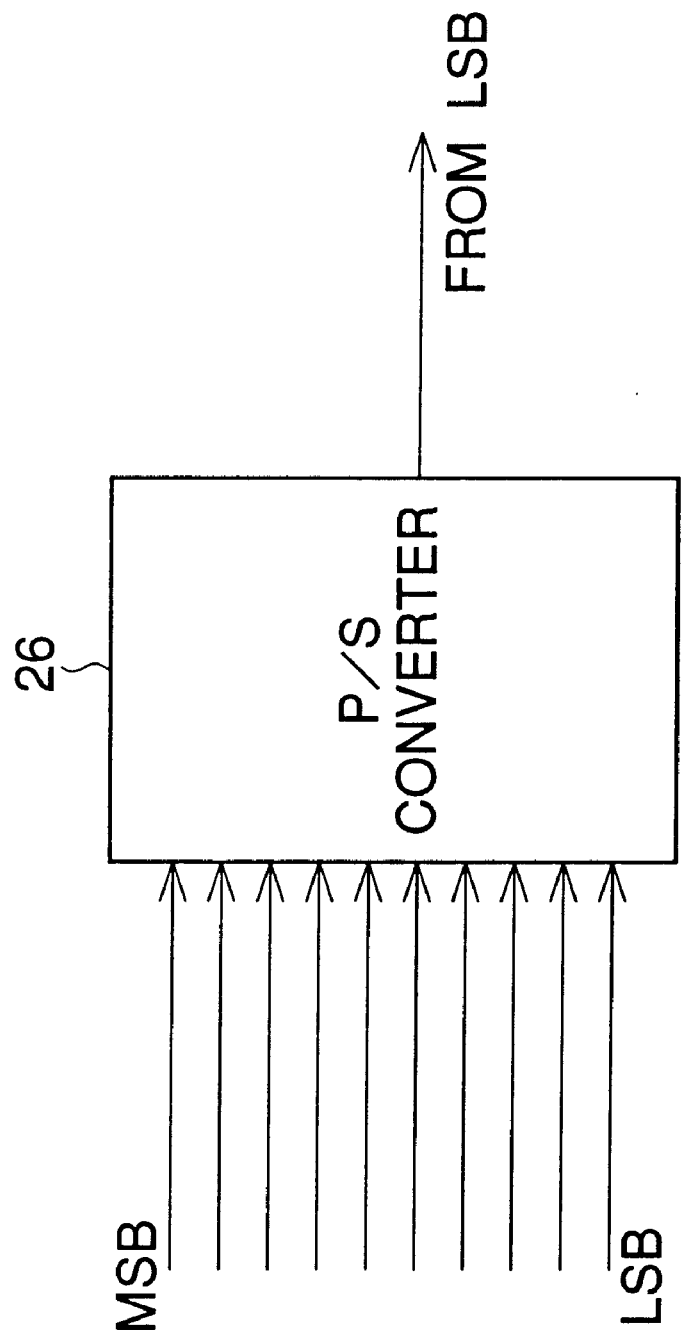
FIG. 4 is a block diagram showing a parallel-to-serial converter used in a digital-conversion processing circuit of the block diagram of FIG. 2.

As shown in FIG. 4, the conversion of the parallel 10-bit digital signal to the serial 10-bit digital signal is carried out in order from the least significant bit (LSB) to the most significant bit (MSB). Namely, the serial 10-bit digital signal is outputted from the P/S converter 26 in such a manner that the least significant bit (LSB) and the most significant (MSB) bit are defined as a leading bit and a trailing bit, respectively.

Figure 5:
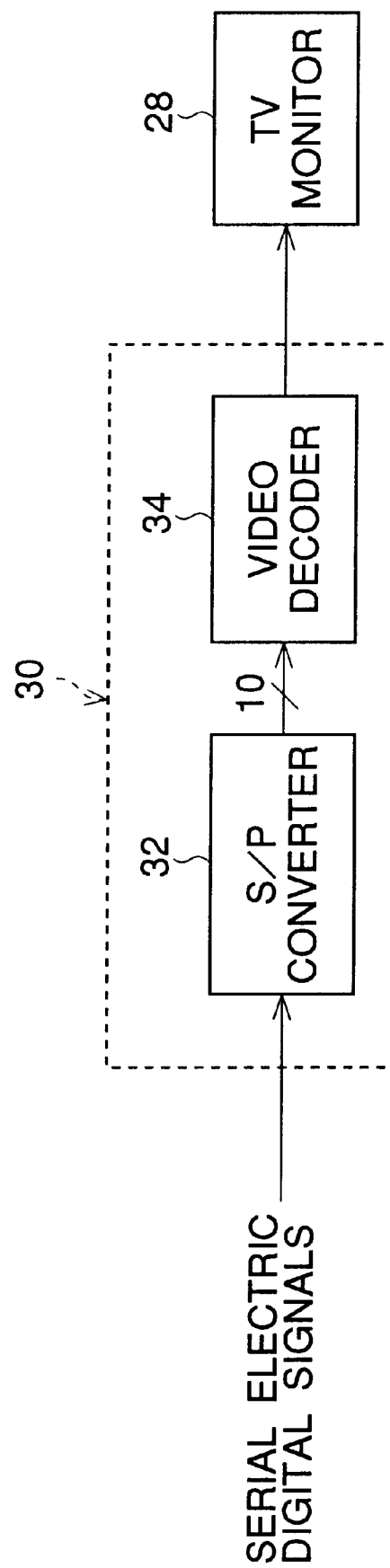
FIG. 5 is a block diagram of an analog-conversion processing device of a TV monitor to be connected to the video-signal processing device of FIG. 2.

FIG. 5 shows a TV monitor 28 as a peripheral equipment, for example, installed at a monitor center of a hospital, and the TV monitor 28 is intended to be connected to the P/S converter 26 of the digital-conversion processing circuit 18 of the video-signal processing device according to the present invention. The system is provided with an analog-conversion processing circuit 30, in which the respective serial digital signals (Y, $C_r$, and $C_b$) fed from the P/S converter 26 thereto are converted into an analog red video signal (R), an analog green video signal (G), and an analog blue video signal (B).

Figure 6:
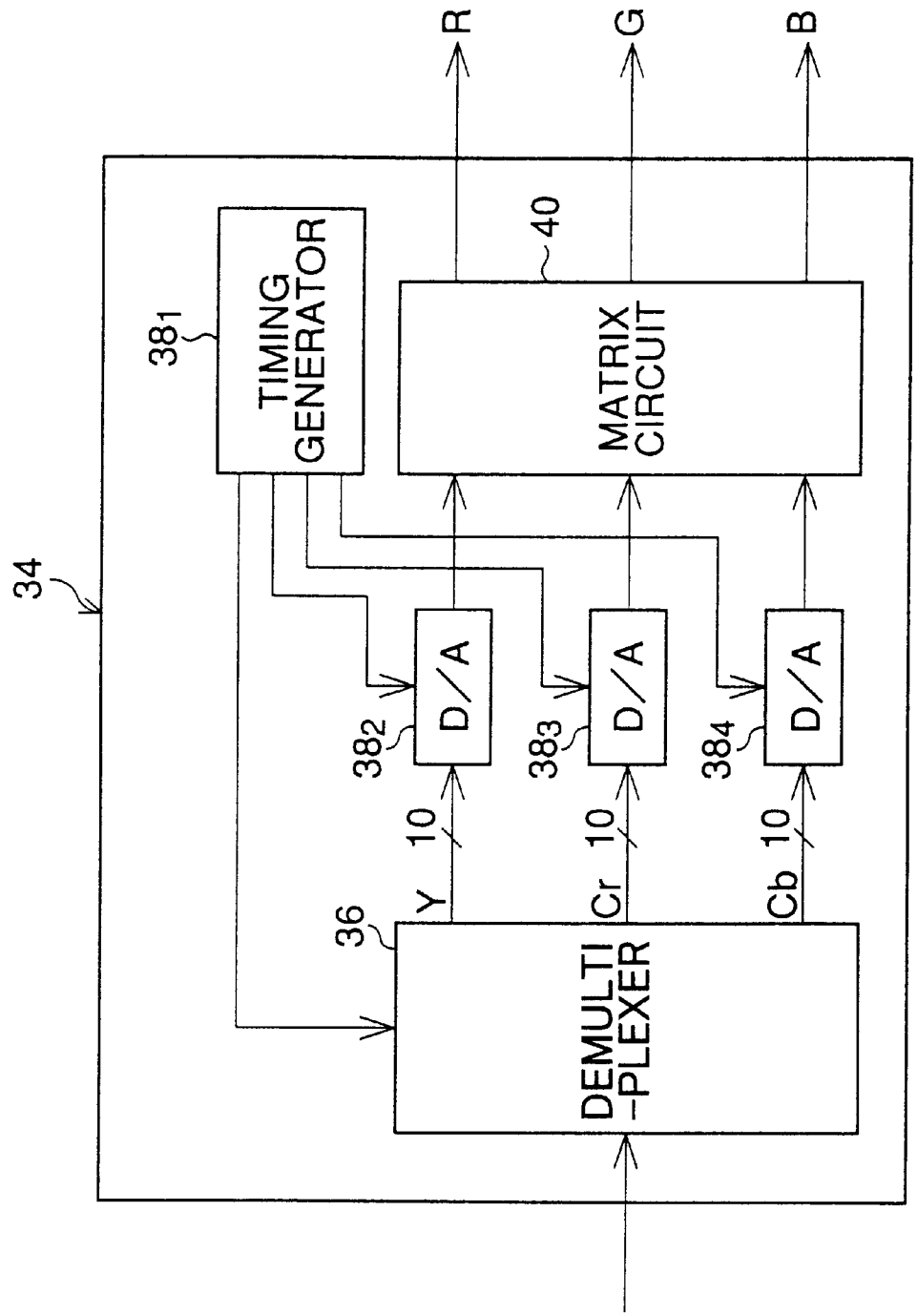
FIG. 6 is a block diagram of a video encoder included in the analog-conversion processing circuit of FIG. 5.

As shown in FIG. 5, the analog-conversion processing circuit 30 comprises a serial-to-parallel (S/P) converter 32 and a video decoder 34. As shown in FIG. 6, the video decoder 34 includes demultiplexer 36; a timing generator circuit $38_1$; digital-to-analog (D/A) converters $38_2$, $38_3$, and $38_4$; and a color-conversion matrix circuit 40.

As it is apparent from the foregoing, the serial 10-bit digital signals (Y, $C_r$, and $C_b$) are sequentially fed from the P/S converter 26 to the analog-conversion processing circuit 30 in the order of the serial 10-bit digital luminance signal (Y), the serial 10-bit color-difference signal ($C_r$), the serial 10-bit digital luminance signal (Y), and the serial 10-bit digital color-difference signal ($C_b$). The serial 10-bit digital signal (Y, $C_r$, $C_b$) fed to the analog-conversion processing circuit 30 is input to the S/P converter 32, which converts the serial 10-bit digital signal (Y, $C_r$, $C_b$) into a parallel 10-bit digital signal (Y, $C_r$, $C_b$).

The parallel 10-bit digital signals (Y, $C_r$, and $C_b$) output from the S/P converter 32 are input to the demultiplexer 36, which distributes the 10-bit digital signals (Y, $C_r$, and $C_b$) to the D/A converters $38_2$, $38_3$, and $38_4$ in such the respective 10-bit luminance signal (Y), 10-bit color-difference signal ($C_r$), and 10-bit color-difference signal ($C_b$) are being input to the D/A converters $38_2$, $38_3$, and $38_4$. The distribution of the 10-bit digital signals (Y, $C_r$, and $C_b$) to the D/A converters $38_2$, $38_3$, and $38_4$ is carried out in accordance with a series of clock pulses having a given frequency, which is output from the timing generator circuit $38_1$.

The respective D/A converters $38_2$, $38_3$, and $38_4$ convert the 10-bit digital signals (Y, $C_r$, $C_b$) into an analog luminance signal (Y), an analog color-difference signal ($C_r$), and an analog color-difference signal ($C_b$), and the conversion of each 10-bit digital signal (Y, $C_r$, $C_b$) into its analog signal is carried out in accordance with a series of clock pulses having a given frequency, which is output from the timing generator circuit $38_1$ to the D/A converters $38_2$, $38_3$, $38_4$.

The analog signals (Y, $C_r$, and $C_b$) output from the respective D/A converters $38_2$, $38_3$, and $38_4$ are input to the color-conversion matrix circuit 40, in which the analog signals (Y, $C_r$, and $C_b$) are converted into an analog red vide signal (R), an analog green video signal (G), and an analog blue video signal (B). These analog color video signals (R, G, and B) are fed from the color-conversion matrix circuit 40 to the TV monitor 28 to thereby reproduce a color image thereon.

Before the reproduction of the color image can be properly carried out on the TV monitor 28, the phase of the outputting frequency of the serial 10-bit digital signal (Y, $C_r$, $C_b$), i.e., the phase of the driving clock pulses for the P/S converter 26 must be coincided with the phase of the composite synchronizing signal (SYNC). To this end, the timing generator circuit $20_1$ is provided with a phase-locked loop (PLL) circuit 42 provided therein.

Figure 7:
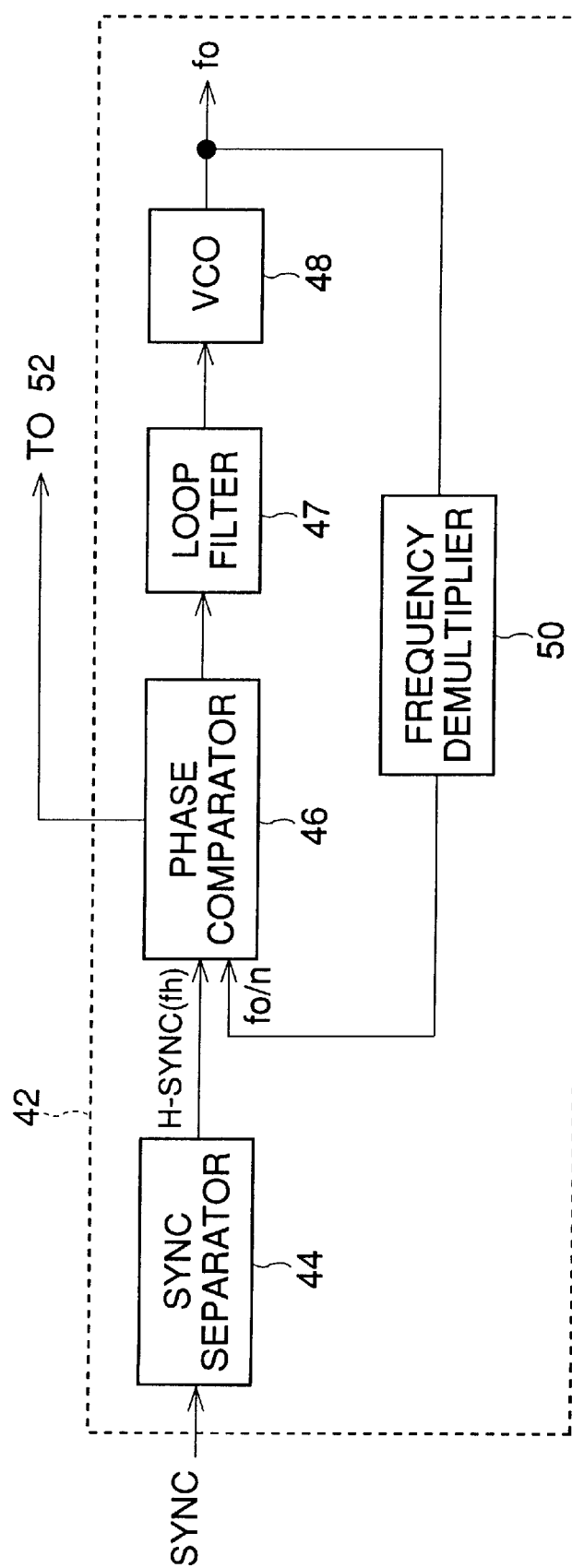
FIG. 7 is a block diagram of a phase-locked loop circuit included in a timing generator circuit shown in FIG. 2.

As shown in FIG. 7, the PLL circuit 42 includes a composite-synchronizing-signal separator 44; a phase comparator 46; a loop filter 47; a voltage controlled oscillator (VCO) 48; and a frequency demultiplier 50. The amplified composite synchronizing signal (SYNC) outputted from the amplifier $16_1$ input to the composite-synchronizing separator 44, in which a horizontal synchronizing signal (H-SYNC) having a given frequency ($f_h$) is separated from the composite synchronizing signal (SYNC). Then, the separated horizontal synchronizing signal (H-SYNC) having the frequency ($f_h$) is input to the phase comparator 46.

On the other hand, the VCO circuit 48 outputs a series of clock pulses having a given frequency ($f_0$), which is divided by the frequency demultiplier 50 into a series of clock pulses having a frequency ($f_0/n$). In this case, "n" is a suitable integer. Then, the series of divided clock pulses having the frequency ($f_0/n$) is input to the phase comparator 46.

At the phase comparator 46, the frequency ($f_h$) of the horizontal synchronizing signal (H-SYNC) is compared with the frequency ($f_0$) of the clock pulses, and a difference between the frequencies ($f_h$ and $f_o$) is output from the phase comparator 46 as a voltage signal representing a phase difference between the horizontal synchronizing signal (H-SYNC) and the divided clock pulses having the frequency ($f_0/n$). Then, the voltage signal is input to the loop filter 47, in which the voltage signal is filtered so as to eliminate high-frequency noises therefrom.

The filtered voltage signal is input to the VCO 48, in which the frequency ($f_0$) of the clock pulses output therefrom is changed on the basis of the input voltage signal in such a manner that the difference between the frequency ($f_h$) of the horizontal synchronizing signal and the frequency ($f_0/n$) of the divided clock pulses decreases. Thus, when a level of the voltage signal output from the phase comparator 46 becomes zero, the phase of the clock pulses output from the VCO 48 coincides with the phase of the horizontal synchronizing signal (H-SYNC), and the frequency ($f_0$) thereof is n (integer) times as many as the frequency ($f_h$) of the horizontal synchronizing signal (H-SYNC).

Note, if the NTSC color system is introduced in the electronic endoscope, the integer "n" is equal to "1,716", and if the PAL color system is introduced in the electronic endoscope, the integer "n" is equal to "1,782".

The series of clock pulses output from the VCO 48 and having a phase coinciding with the phase of the horizontal synchronizing signal (H-SYNC) is input to the P/S converter 26 as the driving clock pulses for the operation thereof. In particular, the series of clock pulses input to the P/S converter 26 is further divided into a series of clock pulses having a frequency which is 10×n times as many as the frequency ($f_h$) of the horizontal synchronizing signal (H-SYNC), and the conversion of the parallel 10-bit digital signal (Y, $C_r$, $C_b$) into the serial 10-bit digital signal is carried out on the basis of the series of clock pulses having a frequency which is 10×n times the frequency ($f_h$) of the horizontal synchronizing signal (H-SYNC), due to the serial feeding of the 10-bit digital signal (Y, $C_r$, $C_b$). Thus, the proper reproduction of the color image on the TV monitor 28 can be ensured.

As it is apparent from FIGS. 2 and 7, the phase comparator 46 is connected to a phase-lock detection circuit 52 that monitors whether or not the level of the voltage signal output from the phase comparator 46 becomes zero. Namely, the phase-lock detection circuit 52 detects a phase-lock, i.e., a coincidence of the phase of the divided clock pulses with the phase of the horizontal synchronizing signal (H-SYNC). For example, when the level of the voltage signal output from the phase comparator 46 becomes zero, i.e., when the phase-lock is obtained in the phase comparator 46, a phase-lock voltage signal output from the phase comparator 46 to the phase-lock detection circuit 52 is changed from a low level to a high level.

As shown in FIG. 2, the phase-lock detection circuit 52 is connected to a signal-output control circuit 54, and a detection voltage signal is output from the phase-lock detection circuit 52 to the signal-output control circuit 54. When the phase-lock detection circuit 52 detects the change of the phase-lock voltage signal from the low level to the high level, it changes the detection voltage signal from a low level to a high level.

The signal-output control circuit 54 is connected to the P/S converter 26, and a disabling/enabling voltage signal is output from the signal-output control circuit 54 to the P/S converter 26. When the detection voltage signal output from the phase-lock detection circuit 52 to the signal-output control circuit 54 is changed from the low level to the high level, the disabling/enabling voltage signal is also changed from a low level to a high level.

In short, if the phase-lock detection circuit 52 does not detect the phase-lock, the disabling/enabling voltage signal is kept at the low level, and, if the phase-lock detection circuit 52 detects the phase-lock, the disabling/enabling voltage signal is kept at the high level.

While the disabling/enabling voltage signal is kept at the low level, the operation of the P/S converter 26 is disabled, whereby the P/S converter 26, does not output a serial digital signal. That is, only while the disabling/enabling voltage signal is kept at the high level, the operation of the P/S converter 26 is enabled, whereby the P/S converter 26 can output the serial digital signal (Y, $C_r$, $C_b$). Accordingly, a turbulent image cannot be reproduced on the TV monitor 28, because the serial digital signals (Y, $C_r$, and $C_b$) cannot be fed to the TV monitor 28 until the phase of the driving clock pulses for the P/S converter 26 coincides with the phase of the horizontal synchronizing signal (H-SYNC). Furthermore, even when the video-signal processing device is connected to the electronic endoscope so that the connection between the signal lines for the composite synchronizing signal (SYNC) is established after the connections between the respective red, green, and blue video signal lines for the red video signal (R), green video signal (G), and blue video signal (B) are established, a turbulent image cannot be reproduced on the TV monitor 28.

As shown in FIG. 2, the video-signal processing device is also arranged such that the first kind of analog color video signal composed of the composite synchronizing signal (SYNC), red video signal (R), green video signal (G), and blue video signal (B), is fed to a suitable peripheral. Namely, the analog composite synchronizing signal (SYNC) amplified by the amplifier $16_1$ is directly output from the video-signal processing device, and the analog red video signal, green video signal, and blue video signal are output from the video-signal processing device through a switch circuit 56 provided therein. The switch circuit 56 is connected to the signal-output control circuit 54, which carries out ON/OFF control of the switch circuit 56 on the basis of a detection voltage signal output from a synchronizing-signal detection circuit 58 connected to the output side of the amplifier $16_1$.

In particular, when the output of the composite synchronizing signal from the amplifier 16 is detected by the synchronizing-signal detection circuit 58, the detection voltage signal output from the synchronizing-signal detection circuit 58 to the signal-output control circuit 54 is changed from a low level to a high level. At this time, an ON/OFF control voltage signal output from the signal-output control circuit 54 to the switch circuit 56 is also changed from a low level to a high level.

While the ON/OFF control voltage signal is kept at the low level, the switch circuit 56 is turned OFF, whereby the output of the analog red video signal, green video signal, and blue video signal from the video-signal processing device is disenabled. While the ON/OFF control voltage signal is kept at the high level, the switch circuit 56 is turned ON, whereby enabling the output of the analog red video signal, green video signal, and blue video signal from the video-signal processing device.

Accordingly, when the video-signal processing device is connected to the electronic endoscope in such a manner that the connection between the signal lines for the composite synchronizing signal (SYNC) is established after the connections between the respective red, green, and blue video signal lines for the red video signal (R), green video signal (G), and blue video signal (B) are established, the feeding of uncontrollable video signals from the video-signal processor device to a peripheral is securely prevented.

As it is apparent from FIG. 2, the respective luminance signal and amplitude-modulated (AM) color-difference signal output from the photo-couplers $14_6$ and $14_7$ are amplified by the amplifiers $16_6$ and $14_7$, and the amplified signals are directly output, as the S-video signal, from the video-signal processing device to a suitable peripheral connected thereto.

Also, the composite color video signal output from the photo-coupler $14_5$ is amplified by the amplifier $16_5$, and the amplified composite color video signal is directly output from the video-signal processing device to a suitable peripheral equipment.

Figure 8:
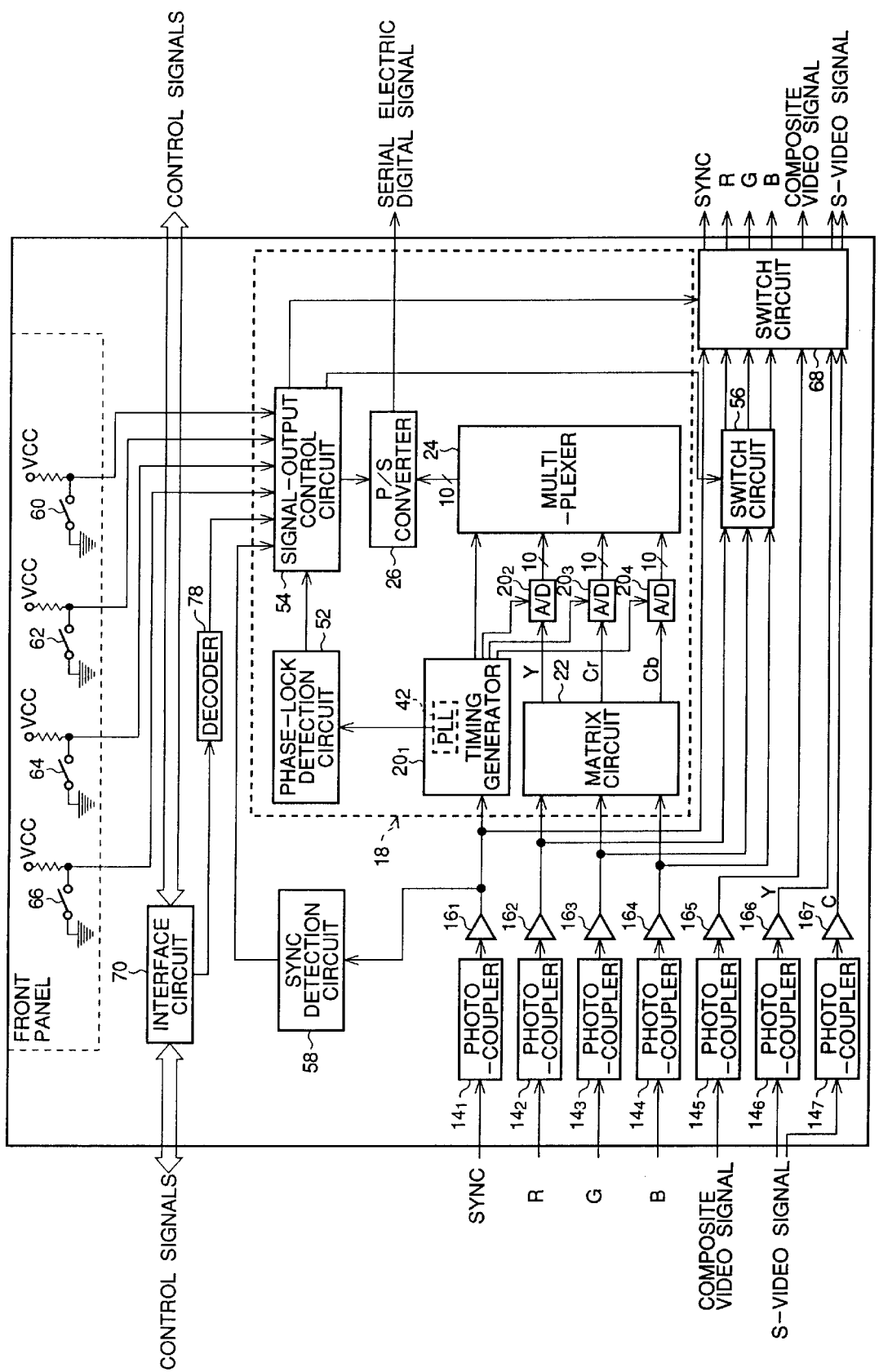
FIG. 8 is a block diagram showing a second embodiment of the video-signal processing device according to the present invention.

FIG. 8 shows a block diagram of a second embodiment of the video-signal processing device according to the present invention. In this drawing, features similar to those of FIG. 2 are indicated by the same reference numerals.

In the second embodiment, the video-signal processing device is provided with four switches 60, 62, 64, 66 provided on a front panel thereof, and each of the switches 60, 62, 64, 66 is manually operated by a user, for example, a doctor operating the system. As illustrated, a first terminal end of each switches 60, 62, 64, 66 is connected to the signal-output control circuit 54, and a second terminal end is grounded. A voltage (VCC) is applied to the first terminal end of each switches 60, 62, 64, 66. When each of the switches 60, 62, 64, 66 is manually closed, the potential (VCC) of the first terminal end is dropped to the ground level.

When the switch 60 is closed to thereby drop the potential (VCC) of the first terminal end to the grounded level, the disabling/enabling voltage signal output from the signal-output control circuit 54 to the P/S converter 26 is forcibly changed from high to low level, even if the phase of the driving clock pulses for the P/S converter 26 coincides with the phase of the horizontal synchronizing signal (H-SYNC). That is, the feeding of the serial digital signals (Y, $C_r$, and $C_b$) from the P/S converter 26 to the TV monitor 28 can be forcibly stopped, if necessary. For example when a user considers a reproduction of a photographed image on the outside TV monitor 28 undesirable, the switch 60 can be closed by the user.

Each of the remaining switches 62, 64, 66 operates a switch circuit 68 via the signal-output control circuit 54. The switch circuit 68 is provided along the signal lines for the component-type color video signal composed of the composite synchronizing signal, red video signal, green video signal, and blue video signal; the S-video signal composed of the luminance signal and amplitude-modulated (AM) color-difference signal; and the composite color video signal combined with the luminance signal and amplitude-modulated color-difference signal.

When the switch 62 is closed to drop the potential (VCC) of the first terminal end to the grounded level, the signal output control circuit 54 operates the switch circuit 68 so that the feeding of the composite synchronizing signal (SYNC), red video signal, green video signal, and blue video signal to a peripheral is forcibly stopped even when the phase of the driving clock pulses for the P/S converter 26 coincides with the phase of the horizontal synchronizing signal (H-SYNC).

Also, when the switch 64 is closed to drop the potential (VCC) of the first terminal end to the grounded level, the signal output control circuit 54 operates the switch circuit 68 so that the feeding of the luminance signal and amplitude-modulated color-difference signal to a peripheral is forcibly stopped. Further, when the switch 66 is closed to drop the potential (VCC) of the first terminal end to the grounded level, the signal output control circuit 54 operates the switch circuit 68 such that the feeding of the composite color video signal to a peripheral is forcibly stopped.

Figure 9:
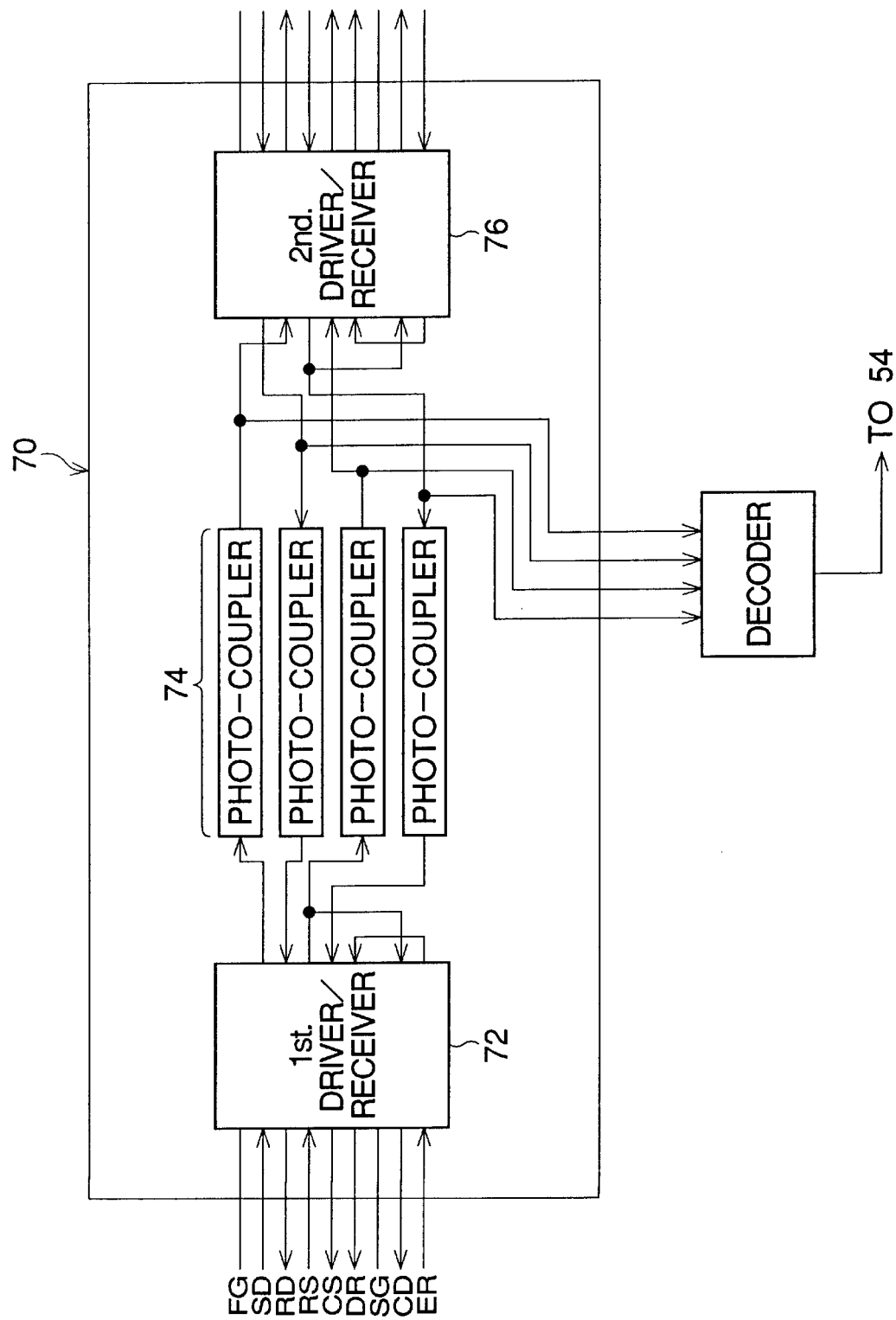
FIG. 9 is a block diagram of an interface circuit provided in the video-signal processing device of FIG. 8.

The video processor 12 of the electronic endoscope may have a plurality of input/output ports for a video-image processing computer. To this end, the second embodiment is provided with an interface circuit 70, which may be arranged as an RS-232C interface. As shown in FIG. 9, the interface circuit 70 includes: a first driver/receiver circuit 72; four photo-couplers 74; and a second driver/receiver circuit 76.

The first driver/receiver circuit 72 is connected to signal lines extending from the video processor 12 of the electronic endoscope indicated by references (FG, SD, RD, RS, CS, RD, SG, CD, and ER). The first driver/receiver circuit 72 is connected to the second driver/receiver circuit 76 via the four photo-couplers 74, and the second driver/receiver circuit 76 is connected to the video-image processing computer through additional signal lines corresponding to the signal lines (FG, SD, RD, RS, CS, RD, SG, CD, and ER). Accordingly, the electronic endoscope is electrically insulated from the video-image processing computer by the photo-couplers 74.

The video-image processing computer may be placed at a place where the electronic endoscope is used, and may be installed at a remote place such as a monitor center of a hospital, remotely located from the place where the electronic endoscope is used. In the latter case, it is preferable to forcibly stop the feeding of the serial digital video signals (Y, $C_r$, and $C_b$) from the video-signal processing device at the monitor center side. For example, there may be a case where a connection of a TV monitor of the monitor center is changed from the video-signal processing device concerned to another video-signal processing device connected to an electronic endoscope used in another place.

To this end, the second embodiment is provided with a decoder 78 connected to the signal-output control circuit 54. When a command signal for stopping the feeding of the serial digital video signals (Y, $C_r$, and $C_b$) from the P/S converter 26 is fed from the video-image processing computer to the video-signal processing device, the command signal is input to the decoder 78 through the interface circuit 70. Upon inputting the command signal to the decoder 78, a voltage signal output from the decoder 78 to the signal-output control circuit 54 is changed from a low level to a high level, whereby the disabling/enabling signal is forcibly changed from the high level to the low level. Thus, the feeding of the serial digital video signals (Y, $C_r$, and $C_b$) from the P/S converter 26 to the TV monitor is forcibly stopped.

The video-signal processing device as mentioned above intervenes between the electronic endoscope and various peripheral equipment such as a TV monitor, a video tape recorder, a printer, a video-image processing computer and so on. The electronic endoscope is electrically insulated from the peripheral equipment by the photo-couplers (14$_1$ to 14$_7$; 74) of the video-signal processing device according to the present invention.

According to the present invention, the serial digital video signals (Y, $C_r$, and $C_b$) output from the digital-conversion processing circuit 18 can be fed to the TV monitor 28 through a coaxial cable having a single signal line, which is cheaper than a parallel signal cable having at least eleven single lines as mentioned above. Also, although the TV monitor 28 is remote from the place where the electronic endoscope is used, a clear and proper reproduction of color images on the TV monitor 28 is ensured, because the video signal is fed to the TV monitor 28 as a digital video signal.

Figure 10:
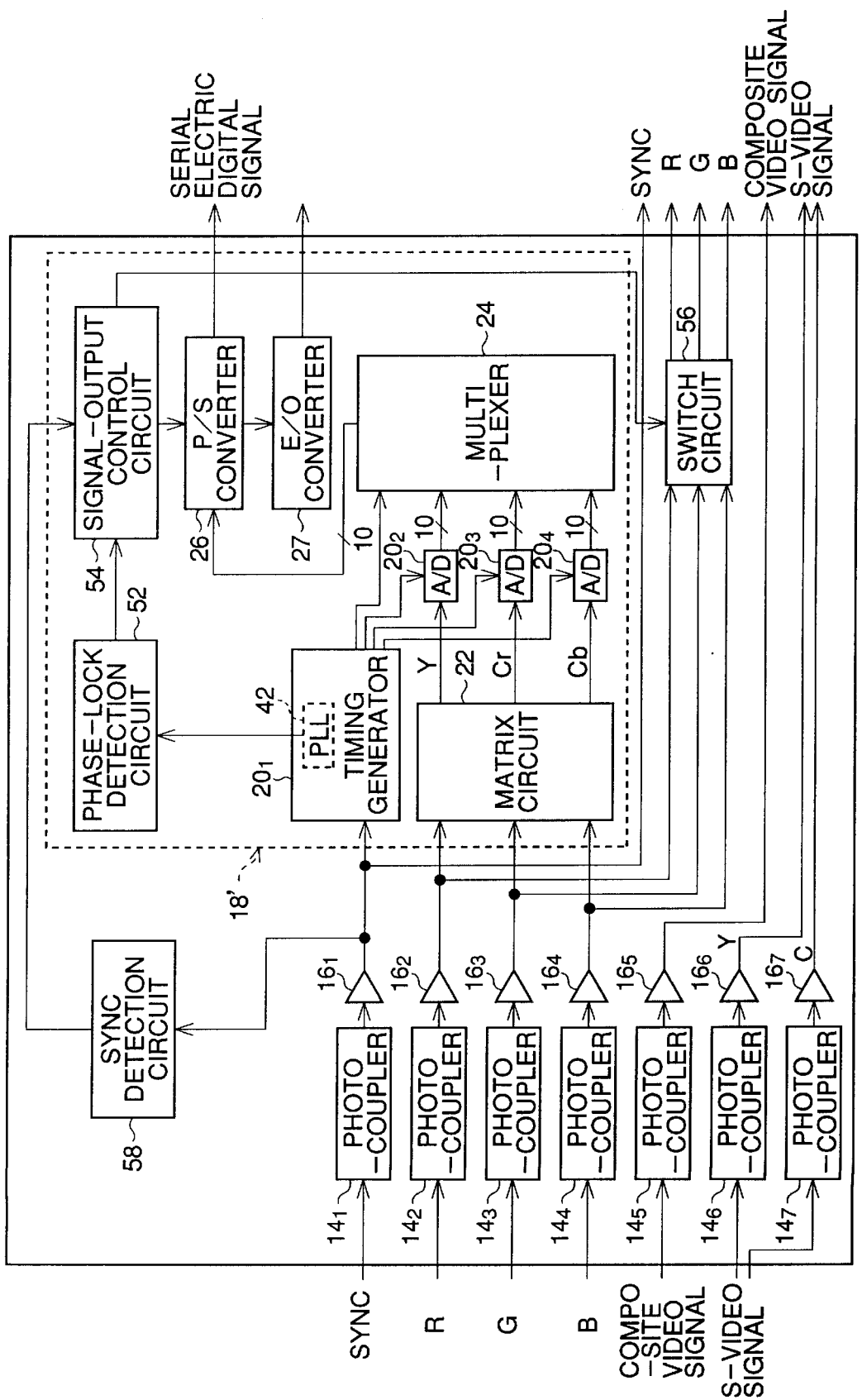
FIG. 10 is a block diagram showing a third embodiment of the video-signal processing device according to the present invention.

FIG. 10 shows a block diagram of a third embodiment of the video-signal processing device according to the present invention. In this drawing, features similar to those of FIG. 2 are indicated by the same reference numerals. The third embodiment is similar to the first embodiment of FIG. 2, except that a digital-conversion processing circuit 18' of the third embodiment further includes an electrical-optical (E/O) converter 27 connected to the P/S converter 26 to convert the respective serial electric digital signals (Y, $C_r$, and $C_b$) into serial optical digital signals (Y, $C_r$, and $C_b$). That is, in the third embodiment, the digital-conversion processing circuit 18 outputs not only serial electric digital signals (Y, $C_r$, and $C_b$) but also serial optical digital signals (Y, $C_r$, and $C_b$).

Figure 11:
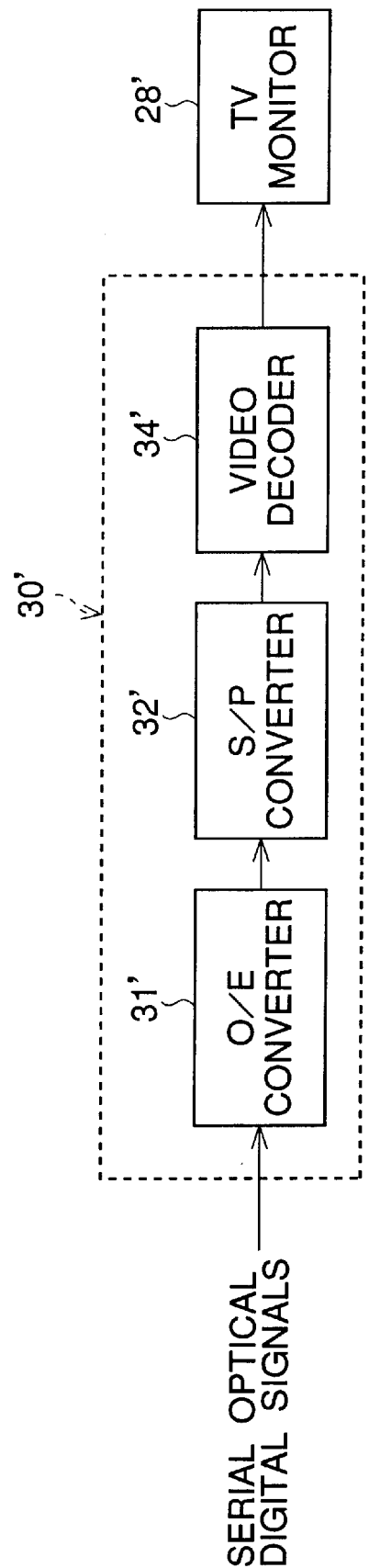
FIG. 11 is a block diagram of an analog-conversion processing circuit of a TV monitor to be connected to the video-signal processing device of FIG. 11.

FIG. 11 shows a TV monitor 28' as a peripheral, which is connected to the E/O converter 27 of the digital-conversion processing circuit 18' through an optical fiber cable. To this end, the TV monitor 28' is provided with an analog-conversion processing circuit 30', in which the respective serial optical digital signals (Y, $C_r$, and $C_b$) fed from the E/O converter 27 along the optical fiber cable are converted into an electric analog red video signal (R), an electric analog green video signal (G), and an electric analog blue video signal (B).

As shown in FIG. 11, the analog-conversion processing circuit 30' comprises an optical-electrical (O/E) converter 31', a serial-to-parallel (S/P) converter 32', and a video decoder 34'. Note, the video decoder 34' is substantially identical with the video decoder 34 shown in FIG. 6.

The serial optical digital signals (Y, $C_r$, and $C_b$) are sequentially fed from the E/O converter 27 to the analog-conversion processing circuit 30' in the order of the serial optical digital luminance signal (Y), the serial optical color-difference signal ($C_r$), the serial optical digital luminance signal (Y), and the serial optical digital color-difference signal ($C_b$). The serial optical digital signal (Y, $C_r$, $C_b$) fed to the analog-conversion processing circuit 30' is input to the O/E converter 31', which converts the serial optical digital signal (Y, $C_r$, $C_b$) into the serial electric digital signal (Y, $C_r$, $C_b$).

The serial electric digital signals (Y, $C_r$, and $C_b$) output from the O/E converter 31' are input to the S/P converter 32', which converts the serial electric digital signals (Y, $C_r$, and $C_b$) into parallel electric digital signals (Y, $C_r$, and $C_b$). These parallel digital signals (Y, $C_r$, and $C_b$) output from the S\P converter 32 are input to the video decoder 34', in which the parallel digital signals (Y, $C_r$, $C_b$) are processed in substantially the same manner as in the video decoder 34 (FIG. 6), the video decoder 34' outputting an analog red video signal (R), an analog green video signal (G), and an analog blue video signal (B) to the TV monitor 28' to reproduce a color image on the TV monitor 28'.

The optical fiber cable feeding the serial optical digital signals (Y, $C_r$, and $C_b$) from the E/O converter 27 to the analog-conversion processing circuit 30' has a signal-feed loss lower than that of the coaxial cable used to feed the serial electric digital signals (Y, $C_r$, and $C_b$) from the P/S converter to the analog-conversion processing circuit 30 (FIG. 5). Accordingly, the third embodiment is preferred when the peripheral equipment such as the TV monitor 28' is more distant from place where the electronic endoscope is used. Also, the peripheral equipment such as the TV monitor 28' can be more securely insulated from the electronic endoscope by the optical fiber cable therebetween.

Figure 12:
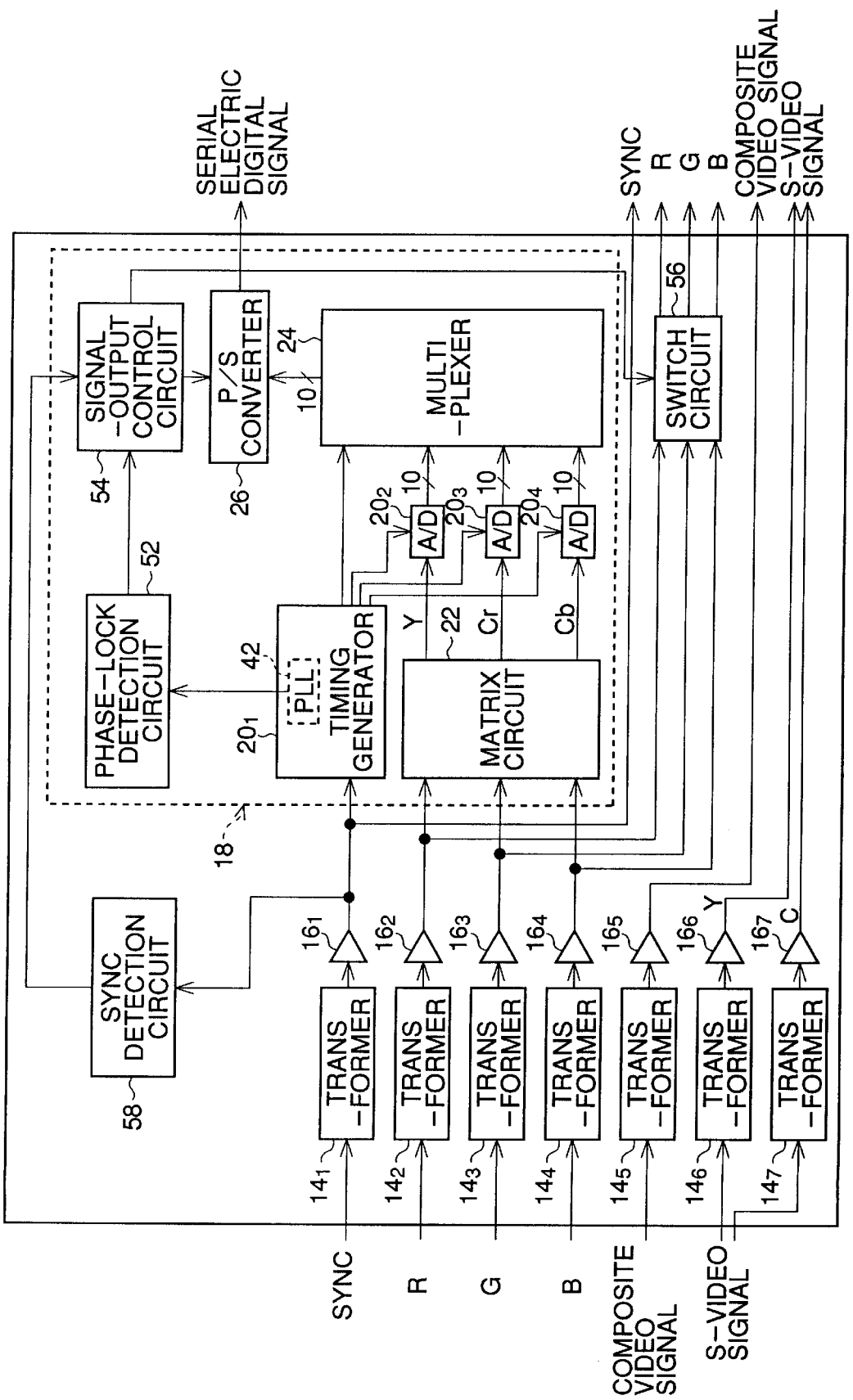
FIG. 12 is a block diagram showing a fourth embodiment of the video-signal processing device according to the present invention.

FIG. 12 shows a fourth embodiment of the video-signal processing device according to the present invention. In this drawing, features similar to those of FIG. 2 are indicated by the same reference numerals. The fourth embodiment is similar to first embodiment of FIG. 2 except that, in a digital-conversion processing circuit 18', seven transformers $14_1'$ to $14_7'$ are substituted for the photo-couplers $14_1$ to $14_7$.

In the fourth embodiment, the respective primary windings of the transformers $14_1'$ to $14_7'$ are connected to the output lines of the video processor 12 of the electronic endoscope, and the respective secondary windings of transformers $14_1'$ to $14_7'$ are connected to the amplifiers $16_1$ to $16_7$. Thus, the electronic endoscope is electrically insulated from the video-signal processing device.

Figure 13:
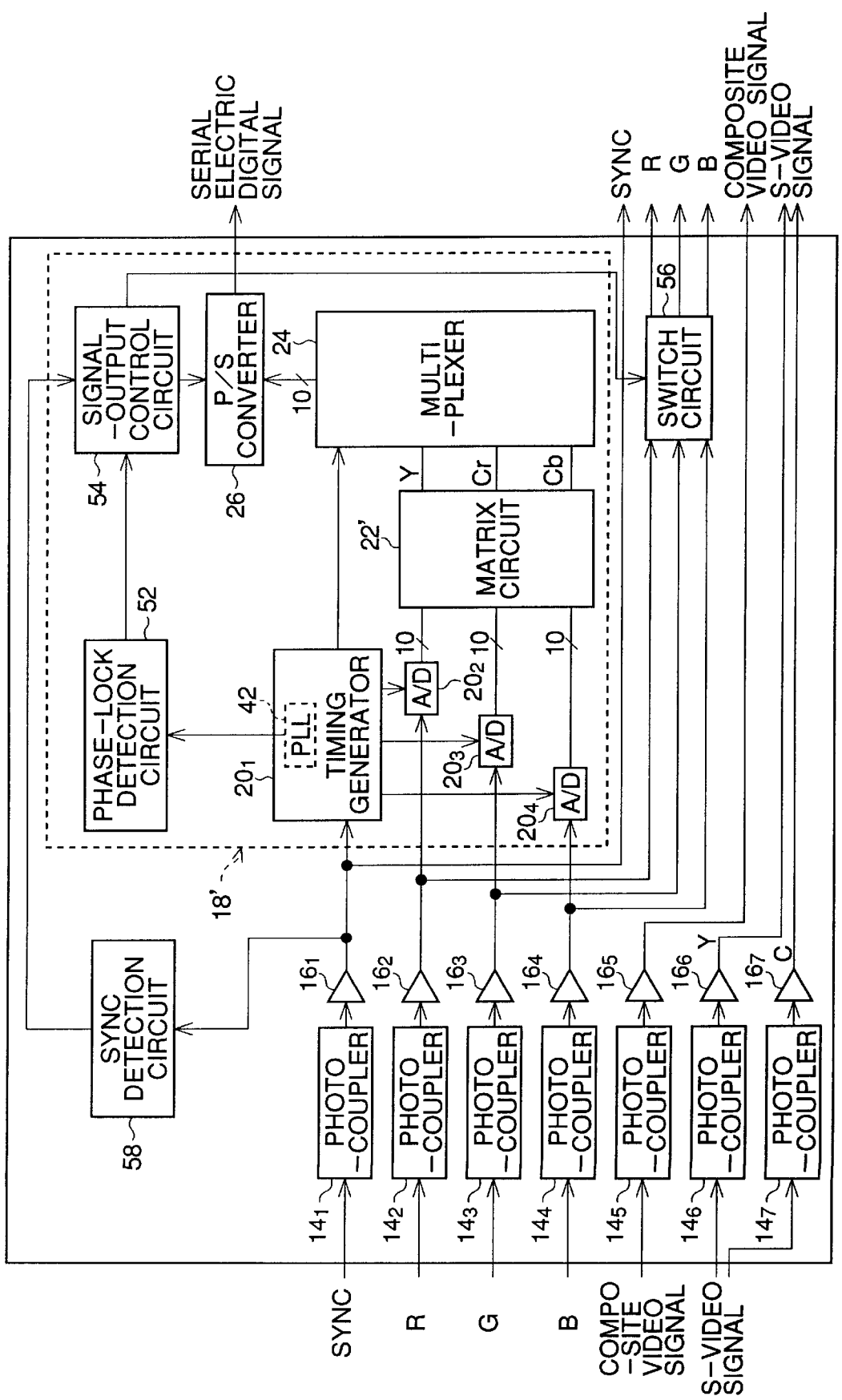
FIG. 13 is a block diagram showing a fifth embodiment of the video-signal processing device according to the present invention.

FIG. 13 shows a fifth embodiment of the video-signal processing device according to the present invention. In this drawing, features similar to those of FIG. 2 are indicated by the same reference numerals. The fifth embodiment is similar to the first embodiment of FIG. 2 except that, in a digital-conversion processing circuit 18', a color-conversion digital matrix circuit 22' is substituted for the color-conversion analog matrix circuit 22, and is disposed between the A/D converters $20_2$ to $20_4$ and the multiplexer 24.

In the fifth embodiment, the respective red video signal (R), green vide signal (G), and blue video signal (B) output from the amplifiers $16_2$ to $16_4$ are input to the A/D converters $20_2$ to $20_4$, which converts the video signals (R, G, and B) into 10-bit digital signals (R, G, and B). Then, the respective 10-bit color digital video signal (R, G, and B) output from the A/D converters $20_2$ to $20_4$ are input to the color-conversion digital matrix circuit $22_1'$, which produces a digital luminance signal (Y), and two kinds of digital color-difference signals $C_r$, $C_b$ ($C_r$=R−Y and $C_b$=B−Y) on the basis of the input color digital video signals (R, G, and B). Thus, the 10-bit digital luminance signal (Y), and the two kinds of 10-bit color-difference signals ($C_r$ and $C_b$) are processed in substantially the same manner as mentioned above.

Figure 14:
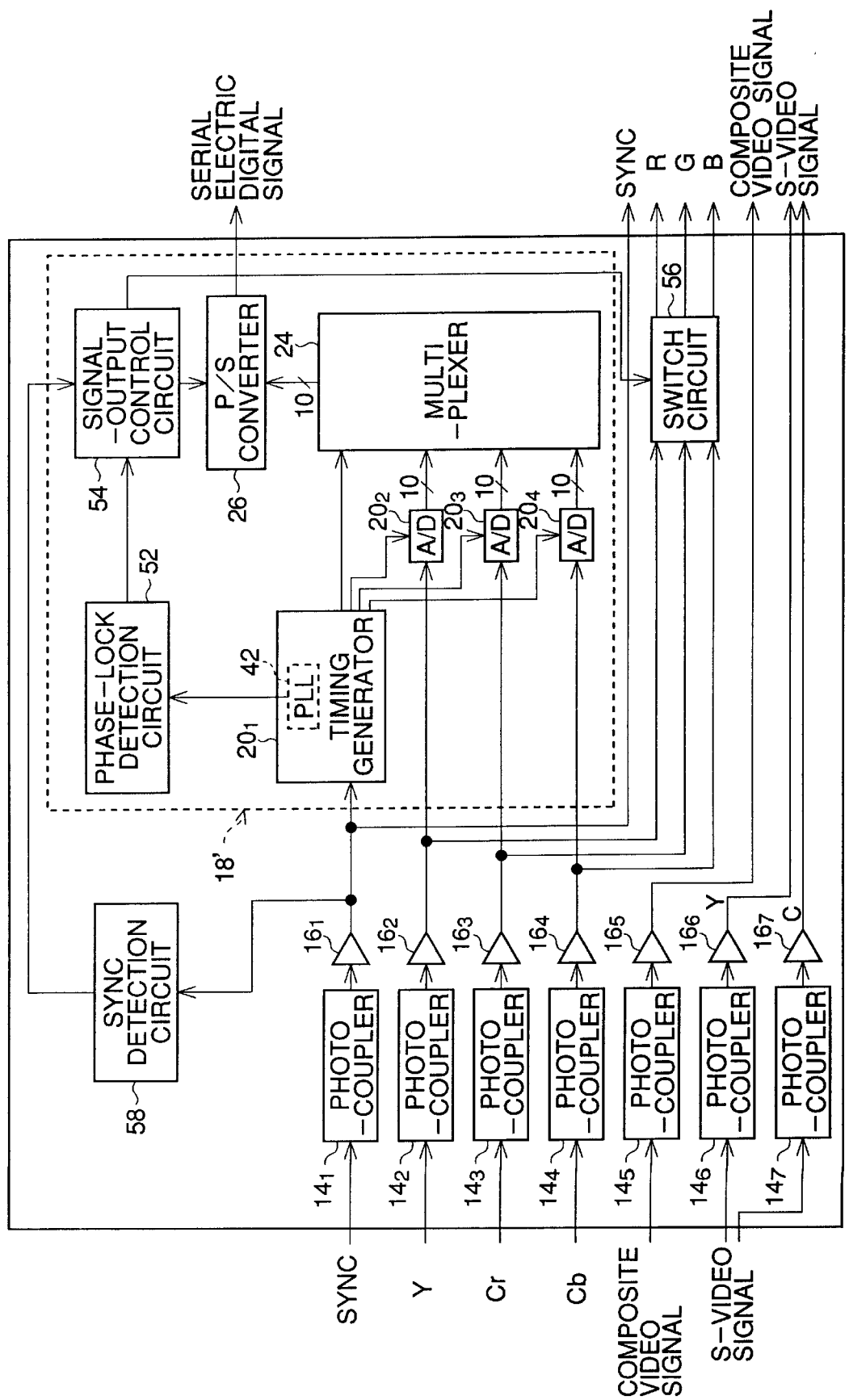
FIG. 14 is a block diagram showing a sixth embodiment of the video-signal processing device according to the present invention.

FIG. 14 shows a sixth embodiment of the video-signal processing device according to the present invention. In this drawing, features similar to those of FIG. 2 are indicated by the same reference numerals. The sixth embodiment is similar to the first embodiment of FIG. 2 except that the color-conversion analog matrix circuit 22 is eliminated from a digital-conversion processing circuit 18'.

The sixth embodiment is connectable to an electronic endoscope that outputs another component type color video signal, including a luminance signal (Y), and two kinds of color-difference signals ($C_r$ and $C_b$), from the video processor thereof. Thus, in the sixth embodiment, the color-conversion analog matrix circuit (22) is unnecessary.

Finally, it will be understood by those skilled in the art that the foregoing description is of preferred embodiments of the device and that various changes and modifications may be made to the present invention without departing from the spirit and scope thereof.

The present disclosure relates to subject matter contained in Japanese Patent Applications No. 8-110269 (filed on Apr. 5, 1996), and No. 8-117086 (filed on Apr. 15, 1996), which are expressly incorporated herein, by reference, in their entireties.

What is claimed is:

1. A video-signal processing device connectable to an electronic endoscope that outputs a component-type electric analog color video signal as at least one kind of video signal, the component-type electric analog color video signal being composed of a composite synchronizing signal-component, and at least three kinds of video-signal-components, said device comprising:

an analog-to-digital converter for converting the video-signal-components into parallel electric digital video-signal-components;

a parallel-to-serial converter for converting the parallel electric digital video-signal-components into serial digital video-signal-components and for outputting the serial digital video-signal-components in accordance with a series of clock pulses;

a phase-locked loop circuit for coinciding a phase of the clock pulses with a phase of the composite synchronizing signal component of the component-type electric analog color video signal;

a phase-lock detector for detecting the coincidence of the phase of the clock pulses with the phase of the composite synchronizing signal; and a signal-output stopper for stopping the outputting of the serial digital video-signal-components from said device until said phase-lock detector detects the coincidence of the phase of the clock pulses with the phase of the composite synchronizing signal, whereby the serial digital video-signal-components are output at proper timing from said device to a compatible external peripheral.

2. A video-signal processing device as set forth in claim 1, further comprising an electrical-optical converter for converting the serial electric digital video-signal-components into serial optical digital video-signal-components.

3. A video-signal processing device as set forth in claim 1, further comprising a manual switch for forcibly stopping the outputting of the serial video-signal-components from said device.

4. A video-signal processing device as set forth in claim 1, further comprising an insulation coupler for making it possible to input the component-type electric analog color video signal from the electronic endoscope to said device, whereby the electronic endoscope is electrically insulated from the peripheral equipment.

5. A video-signal processing device as set forth in claim 4, wherein said insulation coupler is a photo-coupler.

6. A video-signal processing device as set forth in claim 4, wherein said insulation coupler is a transformer coupler.

7. A video-signal processing device connectable to an electronic endoscope that outputs a component-type electric analog color video signal as at least one kind of video signal, the component-type electric analog color video signal beings composed of a composite synchronizing signal-component, a red video-signal-component, a green video-signal-component, and a blue video-signal-component, said device comprising:

a color-conversion analog matrix circuit for producing a luminance signal component, and two kinds of color-difference signal components on the basis of the red, green, and blue video-signal-components;

an analog-to-digital converter for converting each of the luminance signal-component and two kinds of color-difference signal components into parallel electric digital video-signal-components;

a parallel-to-serial converter for converting the parallel electric digital video-signal-components into serial digital video-signal-components and for outputting the serial digital video-signal-components in accordance with a series of clock pulses;

a phase-locked loop circuit for coinciding a phase of the clock pulses with a phase of the composite synchronizing signal component of the component-type electric analog color video signal, a phase-lock detector for detecting the coincidence of the phase of the clock pulses with the phase of the composite synchronizing signal; and a signal-output stopper for stopping the outputting of the serial digital video-signal-components from said device until said phase-lock detector detects the coincidence of the phase of the clock pulses with the phase of the composite synchronizing signal, whereby the serial digital video-signal-components are output at proper timing from said device to a compatible external peripheral.

8. A video-signal processing device as set forth in claim 7, further comprising an electrical-optical converter for converting the serial electric digital video-signal-components into serial optical digital video-signal-components.

9. A video-signal processing device as set forth in claim 7, further comprising a manual switch for forcibly stopping the outputting of the serial video-signal-components from said device.

* * * * *